US006689394B2

(12) United States Patent
Van Scoik et al.

(10) Patent No.: US 6,689,394 B2
(45) Date of Patent: Feb. 10, 2004

(54) REMOVAL OF ECTOPARASITES

(75) Inventors: Kurt G. Van Scoik, Germantown, TN (US); Marcia S. Schlesinger, Germantown, TN (US); Frank A. Anthony, Memphis, TN (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 0 days.

(21) Appl. No.: 09/878,700

(22) Filed: Jun. 11, 2001

(65) Prior Publication Data
US 2003/0003161 A1 Jan. 2, 2003

(51) Int. Cl.⁷ .............. A61K 7/00; A61K 7/06; A61K 33/04; A01N 59/02
(52) U.S. Cl. .............. 424/709; 424/DIG. 10; 514/875; 514/880; 514/881; 514/919; 514/937; 514/944
(58) Field of Search .............. 424/641, 642, 424/677–682, 697, 709, 718, 720, 723, DIG. 10; 514/875, 880, 881, 919, 937, 944

(56) References Cited

U.S. PATENT DOCUMENTS

| 2,349,183 | A | 5/1944 | Mahler ............ 21/87 |
| 3,250,680 | A | 5/1966 | Menkart et al. ....... 167/85 |
| 4,379,143 | A | 4/1983 | Sherry et al. ........ 424/154 |
| 4,626,550 | A | 12/1986 | Hertzenberg .......... 514/770 |
| 5,858,383 | A | 1/1999 | Precopio ............. 424/405 |
| 6,139,859 | A | 10/2000 | Precopio ............. 424/406 |
| 6,265,384 | B1 | 7/2001 | Pearlman ............. 514/31 |
| 6,303,581 | B2 | 10/2001 | Pearlman ............. 514/31 |

FOREIGN PATENT DOCUMENTS

| DE | 198 19 856 | | 11/1999 |
| GB | 2312620 | * | 11/1997 |
| NL | 1010381 | * | 4/2000 |
| WO | WO 99/18800 | | 4/1999 |

OTHER PUBLICATIONS

WPIDS Abstract, accession No. 2000–449754 (2000).*
Retail Pharmacy News—Head Lice, Aug. 2000.*
WPIDS (Derwent) abstract, accession No. 2001–025573, abstracting CN 1268350 (Oct. 2000).*
PROMT abstract, accession No. 2000–720052, abstracting Chain Drug Review, vol. 22 (12), pp. RX7 (Jul. 2000).*

* cited by examiner

Primary Examiner—John Pak
(74) Attorney, Agent, or Firm—Robert A. Franks

(57) ABSTRACT

Ectoparasites, such as fleas, ticks, mites and lice, are removed from a human or animal host after applying a composition to the affected area that causes desiccation of the organism. In one embodiment, treatment is effected by applying a substantially anhydrous composition that has a strong affinity for water. As the composition hydrates, it desiccates the pests and facilitates their mechanical removal, such as by combing.

9 Claims, No Drawings

REMOVAL OF ECTOPARASITES

INTRODUCTION TO THE INVENTION

The present invention relates generally to the removal of ectoparasites from the bodies of humans and animals, and more particularly to a topical treatment to facilitate such removal.

Ectoparasitic infestation of humans and animals is a serious health problem throughout the world. Of particular importance as a public health issue is pediculosis, or infestations with lice, which are pervasive among children and can quickly be spread in a school setting. A very common parasite is *Pediculus humanus* var *capitis*, the common head louse, although there are other important parasites, including *Pthirus pubis* (the pubic louse) and *Pediculus humanus* var *corporis* (the body louse). Infestations are frequently accompanied by itching and skin damage. Infections may occur when the skin is scratched in an attempt to relieve the itching. Further, lice are known to be capable of transmitting serious diseases, including trench fever, relapsing fever and typhus.

Pediculosis is most frequently treated by applying pesticidal compositions, such as lotions or shampoos, to the affected body areas, such as the hair, and then exhaustively combing with a fine-toothed comb made especially for the purpose of removing nits. Commercially available preparations may include as their active ingredients pyrethrins, piperonyl butoxide, malathion, lindane or permethrins, many of which unfortunately have neurotoxic properties, are readily absorbed through the skin and therefore can establish undesirable systemic concentrations. It is perceived that the effectiveness of pesticides has recently diminished, as the parasites appear to continually become more resistant to their action. The resistance may be aggravated by small amounts of residual pesticide on the treated areas, following the procedure. This resistance also contributes to an increased opportunity for toxic systemic exposure to the active ingredients, since the preparations must be applied repeatedly to obtain an eradication of the infestation. Further, the pesticides do not usually kill the parasite's eggs that may be present on a host, so the tedious mechanical removal techniques must also be used.

DiNapoli et al., "Eradication of Head Lice with a Single Treatment," *American Journal of Public Health*, Vol. 78, pages 978–980, 1988, reported a study in which 7 percent of patients treated with a commercial 1 percent permethrin cream rinse, and 16 percent of patients treated with a commercial product containing 0.3 percent pyrethrins, 3 percent piperonyl butoxide, 1.2 percent petroleum distillate and 2.4 percent benzyl alcohol, experienced adverse reactions including pruritis, erythema, tingling, rash and other conditions. Further, by 14 days following treatment 38 percent of the patients treated with the pyrethrin product were found to host live lice, considered a treatment failure. Permethrin is described as having residual activity on the hair for up to two weeks.

R. J. Roberts et al., "Comparison of Wet Combing with Malathion for Treatment of Head Lice in the UK: a Pragmatic Randomised Controlled Trial," *The Lancet*, Vol. 356, pages 540–544, 2000, report that mechanical removal of lice with a commercial comb every 3–4 days for two weeks gave a "cure" rate of only 38 percent, while two treatments with 0.5 percent malathion lotion seven days apart gave a "cure" rate of 78 percent.

Published results for the various topical pesticidal treatments were compared by. R. H. Vander Stichele et al., "Systematic Review of Clinical Efficacy of Topical Treatments for Head Lice," *British Medical Journal*, Vol. 311, pages 604–608, 1995. It was concluded that only permethrin had sufficient evidence of efficacy.

There are other approaches to treating the infestations, including the application of heavy, oily substances such as mineral oil, petrolatum, mayonnaise and the like in an attempt to suffocate the ectoparasites, but these have not been found particularly effective, esthetically pleasing or convenient. One major disadvantage of such treatments is the prolonged time (usually several hours) required to achieve suffocation, after the agent has been applied.

The suffocation technique has been refined, such as by the approach of U.S. Pat. No. 6,139,859 to Precopio which utilizes air-impermeable water-dispersible liquid compositions containing surface active agents. Another type of treatment refinement is the technique of Pearlman et al. in PCT International Publication WO 99/18800, involving the topical application of surfactant substances as "pediculostatic agents" which immobilize the parasites to permit their removal by combing.

It remains desirable to have a treatment for ectoparasitic infestations which is efficacious, acts rapidly and does not generate great discomfort or require any exposure of the host to toxic agents.

SUMMARY OF THE INVENTION

The present invention is a treatment for ectoparasitic infestations, particularly those involving fleas, ticks, mites or lice, comprising establishing environmental conditions whereby systemic moisture is removed from the ectoparasites, for a time sufficient to cause immobilization or death of the ectoparasites, then removing the pests by mechanical means such as combing.

This invention involves topical applications of compositions containing active ingredients which have a strong affinity for water, such as is present in organisms such as ectoparasites. Contact of the organisms with the active agents causes desiccation which results in immobilization and/or mortality of the parasites, facilitating their mechanical removal by combing and other techniques. In many instances, the active agents also change the microenvironmental pH conditions; this can also have a significant adverse effect on mobility of the organisms and viability of their eggs.

Treatment of ectoparasites can be conducted using a composition which generates a strong hydration reaction, when contacted with water. In one embodiment, the composition is a particulate solid, a semi-solid or a fluid containing substantially no aqueous matter, or in some instances only a small amount of water, and which contains a particulate inorganic substance that undergoes a strong hydration reaction in the presence of water. Examples of suitable substances are salts of alkali metals and alkaline earth metals. The hydration reaction is not necessarily one which results in formation of any new chemical compound, but can be an absorption-type reaction, and may be exothermic, endothermic or not involve any significant temperature changes.

DETAILED DESCRIPTION OF THE INVENTION

The invention will be described primarily as it relates to the reduction of human head lice infestations, although those skilled in the art will recognize its applicability to other ectoparasites and animal subjects, and the inventors intend that their invention will have such applicability.

In the following description and the claims, it is intended that a reference to a percentage means percent by weight, unless the context clearly indicates otherwise. Since the chemical names for certain composition ingredients are quite cumbersome, some ingredients are identified herein by their adopted names as given in standard reference works, including J. A. Wenninger et al, Eds., *International Cosmetic Ingredient Dictionary and Handbook*, 8$^{th}$ Ed., The Cosmetic, Toiletry and Fragrance Association, Washington, D.C., 1999.

Lice egg cases ("nits") are thought to be attached to hair by means of mucopolysaccharide adhesive substances. Removal of the nits therefore requires a very thorough combing operation, and is not appreciably facilitated by many of the usual pesticide treatments. However, embodiments of the present invention provide both desiccation and a changed pH in the microenvironment of the nit, which can alter the physical and chemical nature of the egg casing itself. The provision of lubricious agents in a composition also can facilitate lice and nit removal by combing.

Suitable active agents for use in the present invention are generally those salts of alkali metals, ammonium ions, alkaline earth metals and transition metals that have a strong affinity for water. Examples of useful substances include one or more of lithium chloride, sodium chloride, sodium nitrate, sodium sulfate, potassium chloride, potassium nitrate, potassium sulfate, ammonium chloride, ammonium nitrate, magnesium chloride, magnesium nitrate, calcium chloride, calcium bromide, calcium nitrate, calcium sulfate, strontium chloride, strontium nitrate and zinc chloride. This listing is not intended to be exhaustive, as many other substances can be used. The compounds will be used in their anhydrous or substantially anhydrous forms, and mixtures of any two or more active agents can be used.

When an active ingredient is placed in contact with water, such as that contained in moistened hair, in the immediate vicinity of an ectoparasite or the egg of an ectoparasite, a desiccating microenvironment is created. Depending on the chemical nature of the active ingredient, there may also be a change in pH and/or a localized change in temperature. All of these environmental changes are detrimental to the viability of the ectoparasite and its eggs. The result will ideally be death of the ectoparasite and eggs, but in some instances inhibition of the mobility of the pest will be the primary effect. In any event, it will typically be necessary to remove the dead and immobilized organisms, and the eggs, by combing or other mechanical means.

In its least complicated embodiment, a desiccating composition for ectoparasite removal can contain only a solid particulate active ingredient or mixture of active ingredients, preferably in the form of finely divided particles. However, in many instances it will be desired to include other components, such as up to about 50 percent of inactive particulate fillers, diluents or extenders, such as talc, cornstarch and the like, to promote more uniform coverage of the area to which the composition is applied. These dry compositions can also include solid surfactants, so that the product can be easily removed following a treatment by merely adding water to form a cleansing environment (such as a shampoo) and then rinsing the treated area with additional water.

More typically, the composition will be fluid, such as in the form of a suspension or lotion containing about 1 to about 50 percent of the active ingredient or mixture of active ingredients, since such product forms are generally more easily applied.

Useful fluid desiccating compositions can be prepared by suspending, or in some instances dissolving, an active ingredient or mixture of active ingredients in a substantially anhydrous liquid vehicle such as: a hydrocarbon, including light and heavy mineral oils; a glycol such as a polyethylene glycol, propylene glycol or triethylene glycol; glycerol; and the like. Use of the glycols is presently preferred, since they can also act as desiccating agents. Typical concentrations of the vehicle range from about 1 to about 60 percent.

Optionally, a suspending agent may be present in a fluid desiccating composition to maintain a stable dispersion. Useful agents include, without limitation, fumed silica and polyvinylpyrrolidone having molecular weights from about 25,000 to about 100,000, in amounts about 0.1 to about 2 percent.

The compositions may further include other components, such as surfactants, lubricants, texture modifiers, acidifiers and/or preservatives.

Useful optional surfactants include, without limitation, sodium lauryl sulfate, sorbitan laurate, mixtures of glyceryl stearate and PEG-100 stearate, methyl gluceth-10, methyl gluceth-40, sorbitan palmitate, polysorbate 20, polysorbate 80, steareth-2 and many others. The surfactants will be present in amounts about 0.1 to about 16 percent, and can create shampoo-type products which are easily removed after the ectoparasite treatment is completed.

The lubricants that can be incorporated are represented by dimethicone, simethicone and other silicone-type materials, and act to lubricate and condition the hair, as well as facilitate passage of a comb through the hair. Useful concentrations, when this component is present, are about 0.1 to about 2 percent.

Optional texture modifiers that may be included are exemplified by stearic acid, cetyl alcohol, PEG-180, polyethylene glycol 1450 and polyethylene glycol 3350, in amounts about 0.1 percent to about 5 percent.

It may be desired to incorporate a pH-adjusting ingredient in the composition, if the hydrated active ingredient tends to establish excessively acidic or alkaline conditions (such as pH values which are less than about 4 or greater than about 9). Optional acidifiers that may be used include, without limitation, benzoic acid, citric acid and stearic acid. Useful optional alkalizers include, without limitation, calcium hydroxide, magnesium hydroxide and organic bases such as triethanolamine. The pH adjusters, when used, will generally be present in amounts about 0.1 percent to about 2 percent, as needed to obtain a desired bulk pH condition.

As an alternative to incorporating a pH adjusting ingredient, suitable bulk pH conditions can frequently be obtained by incorporating an active ingredient that yields acidic conditions together with another active ingredient which yields alkaline conditions.

Products that are intended for application to the skin frequently are protected against microbial proliferation by the inclusion of a preservative component. Suitable preservatives for use in the present compositions include, without limitation, methylparaben, propylparaben and benzethonium chloride. The preservative, when present, will typically be included in concentrations about 0.05 to about 0.2 percent.

Included within the scope of the present invention is a kit for treating an ectoparasite infestation, including a suitable container filled with a composition that can be applied to an area of the body to cause desiccation of ectoparasites, together with a mechanical device for removing ectoparasites after they are affected by the composition. For compositions that are in the form of a fluid, such as liquids, lotions and creams, the composition can be contained in a bottle or collapsible tube. Aerosol compositions can be contained in the customary dispensing canisters, fitted with a suitable valve for dispensing the product. Powdered compositions can be contained in one of the customary canisters having a perforated cap for shaking out a desired amount, or in a bottle. Many delousing combs are commercially available, being fabricated from plastic substances or metals, and any of these are suitable for inclusion in the kit. It is preferred that the kit be made suitable for a single use, including sufficient composition for one application.

The invention will be further described with reference to the following example, which is not intended to limit the scope of the claimed invention in any manner.

EXAMPLE

A lotion composition for ectoparasite removal is prepared by combining the following components:

| Ingredient | Percent |
| --- | --- |
| Calcium sulfate, anhydrous | 20 |
| Benzoic acid | 2 |
| Fumed silica | 0.3 |
| Cetyl alcohol | 1.5 |
| Polyvinylpyrrolidone | 0.5 |
| Cyclomethicone + Dimethicone copolyol * | 2 |
| Methylparaben | 0.13 |
| Polyethylene glycol | 67 |
| Propylparaben | 0.07 |
| Polysorbate 20 | 5 |
| Stearic acid | 1.5 |

* Dow Corning 3225C Formulation Aid, sold by Dow Corning Corporation, Midland, Michigan U.S.A.

From this description of specific embodiments of the invention, it will be appreciated that the present invention is not limited to those precise embodiments and that various changes and modifications can be effected therein by one of ordinary skill in the art, without departing from the scope or spirit of the invention as defined solely by the appended claims.

What is claimed is:

1. A method for treating an ectoparasitic infestation of an area of a human or animal body, comprising applying a substantially anhydrous composition comprising sodium sulfate to establish a desiccating environment in the area which causes ectoparasites to become immobile or killed and then removing the ectoparasites from the area.

2. The method of claim 1, wherein the ectoparasites comprise *Pediculus humanus* var *capitis*.

3. The method of claim 1, wherein the ectoparasites comprise *Pediculus humanus* var *corporis*.

4. The method of claim 1, wherein the ectoparasites comprise *Pediculus humanus* var *pubis*.

5. The method of claim 1, wherein the ectoparasites comprise fleas, ticks or mites.

6. The method of claim 1, wherein the composition is in the form of a powder.

7. The method of claim 1, wherein the composition is in the form of a semi-solid or fluid.

8. The method of claim 1, wherein immobilized or killed ectoparasites are removed by combing.

9. A method for treating an ectoparasitic infestation of an area of a human or animal body, comprising applying a substantially anhydrous semi-solid or fluid composition comprising sodium sulfate to establish a desiccating environment in the area which causes ectoparasites to become immobile or killed, and then combing to remove ectoparasites from the area.

* * * * *